United States Patent [19]

Orimo et al.

[11] Patent Number: 5,002,968
[45] Date of Patent: Mar. 26, 1991

[54] ACTIVATOR FOR OSTEOBLASTS

[75] Inventors: Hajime Orimo; Hiroshi Satoh; Kohei Miyao, all of Tokyo; Norihiro Kakimoto, Machida, all of Japan

[73] Assignee: ASAI Germanium Research Institute Co., Ltd., Tokyo, Japan

[21] Appl. No.: 276,666

[22] Filed: Nov. 28, 1988

[30] Foreign Application Priority Data

Dec. 7, 1987 [JP] Japan .................................. 62-308982

[51] Int. Cl.⁵ .............................................. A61K 31/28
[52] U.S. Cl. ................................................ 514/492
[58] Field of Search ......................................... 514/492

[56] References Cited

U.S. PATENT DOCUMENTS 4,822,817  4/1989  Orimo et al. ........................ 514/492

FOREIGN PATENT DOCUMENTS 62-252794  11/1987  Japan .
2191697   12/1987  United Kingdom .

OTHER PUBLICATIONS

Chemical Abstracts, vol. 109, No. 15, p. 129305b.

Primary Examiner—Stanley J. Friedman
Assistant Examiner—Kevin Weddington
Attorney, Agent, or Firm—Burns, Doane, Swecker & Mathis

[57] ABSTRACT

The present invention provides (a) an activator for osteoblast comprising, as an active ingredient, a salt between (1) an organogermanium compound represented by the formula (I)

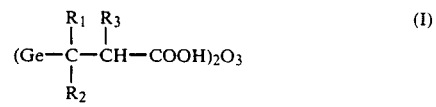

[in the above formula (I), $R_1$, $R_2$ and $R_3$ which may be the same or different, are independently a hydrogen atom, a lower alkyl group such as methyl, ethyl or the like, or an aryl group] and (2) a basic group-containing compound, and (b) a method for activating osteoblasts, which comprises administering in need of such treatment an effective amount of a salt between an organogermanium compound represented by the above formula (I) and a basic group-containing compound.

5 Claims, 3 Drawing Sheets

ACTIVATOR FOR OSTEOBLASTS

BACKGROUND OF THE INVENTION

1. Field of the Invention

The present invention relates to an activator for osteoblasts and more particularly to an activator for osteoblast containing a particular organogermanium compound as an active ingredient and having a strong effect.

2. Description of the Prior Art

Metabolic osteopathy believed to have a connection with calcium metabolism, etc., such as senile osteoporosis, renal osteodystrophy and the like, is increasing year by year. Meanwhile, the pathology and analytical method of said disease which had been unknown previously have been established recently. As a result, metabolic osteopathy is drawing increasing attention in the medical world.

Metabolic osteopathy is said to generally have a close connection with calcium metabolism or its abnormality. Senile osteoporosis, for example, is believed to occur in such a mechanism that abnormal calcium metabolism combined with other factor(s) breaks a bone resorption-osteogenesis balance resulting in reduction in osteogenesis as compared with bone resorption.

In metabolic osteopathy, pain, which is not reactive to ordinary analgesics, is common or bone fractures may occur which are difficult to cure. Thus, there is an urgent need for curing metabolic osteopathy.

Establishment or development of a method and drug for curing metabolic osteopathy has been difficult because metabolic osteopathy does not refer to a single disease but to a group of particular diseases and because the cause for each disease is unknown or explained by various different theories.

Meanwhile, metabolic osteopathy-curing drugs such as calcitonin and active type vitamin D have made appearances recently. However, these drugs have no strong effect, show strong side effects, and are difficult to apply.

SUMMARY OF THE INVENTION

The present invention has been achieved in view of the above described background. The activator for osteoblasts of the present invention is characterized by comprising, as an active ingredient, a salt between (1) an organogermanium compound represented by the formula (I)

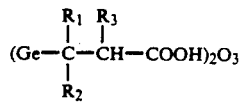

$$(Ge-\underset{R_2}{\underset{|}{C}}-\underset{|}{\overset{R_1}{\overset{|}{}}}\underset{}{\overset{R_3}{\overset{|}{}}}CH-COOH)_2O_3 \quad (I)$$

in the above formula (I), $R_1$, $R_2$ and $R_3$ which may be the same or different, are independently a hydrogen atom, a lower alkyl group such as methyl, ethyl or the like, or an aryl group and (2) a basic group-containing compound.

The present inventors studied in-depth the pathology and causes of metabolic osteopathy and, as a result, developed a theory that the activation of osteoblasts by an appropriate means would effectively cure metabolic osteopathy because the activation would improve, in the case of senile osteoporosis, for example, an imbalance between osteogenesis and bone resorption. Based on this theory, extensive study was undertaken in order to find a compound which can activate osteoblasts, and thus the present invention has been discovered.

The present inventors completed further studies in order to find a compound which, as compared with the compound used in the activator for osteoblasts which had been developed previously by some of the present inventors and for which a patent application had been filed (Japanese Patent Application No. 142198/1986). The present compound has better absorption, a higher absorption ratio and higher bioavailability and has wider applications. As a result, the present invention has been achieved.

DETAILED DESCRIPTION OF THE PREFERRED EMBODIMENTS

Figure 1:
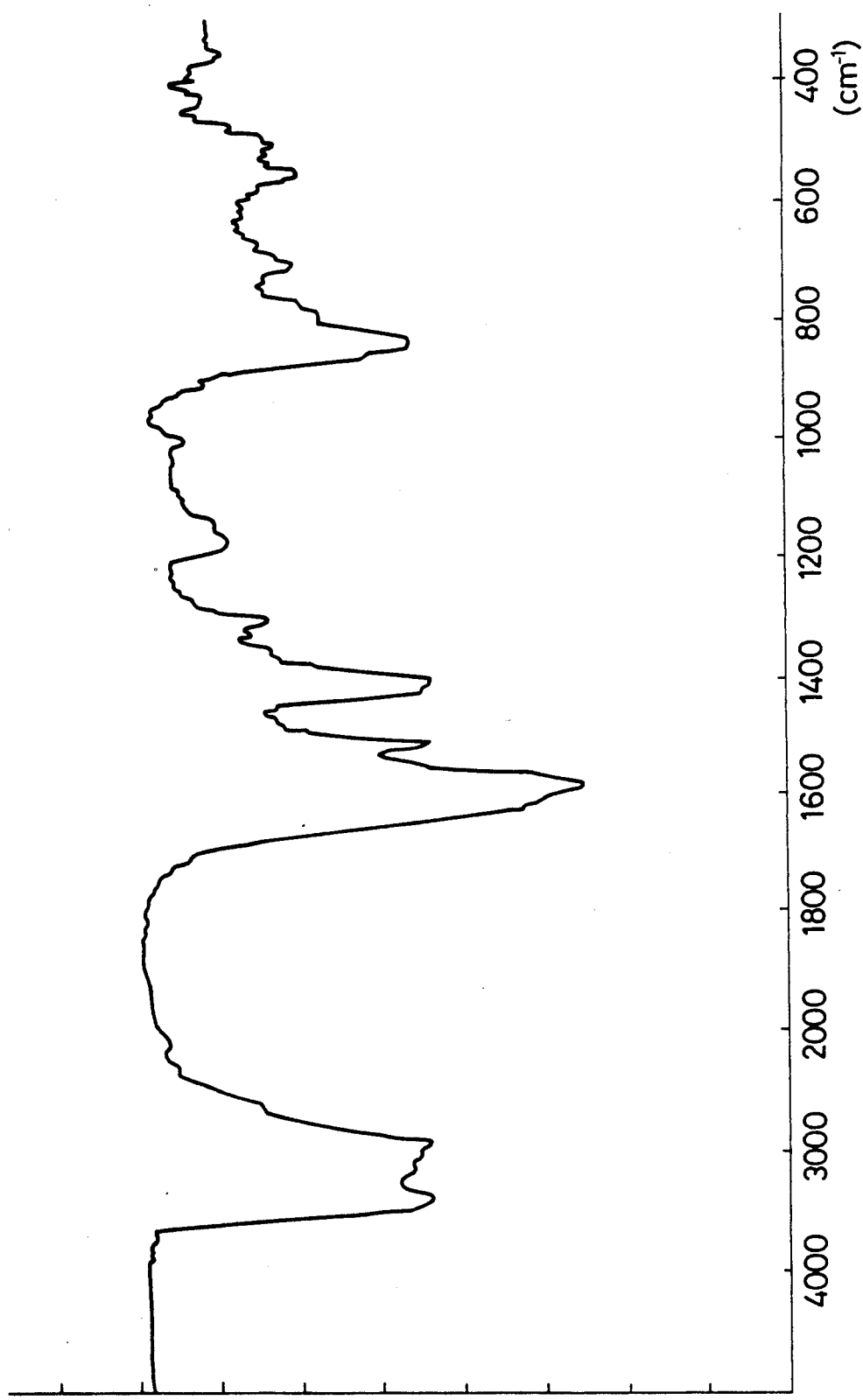
FIG. 1 is an IR spectrum of a salt used in the activator of the present invention.

The present invention is explained in detail below.

Germanium which is known as a metal has been a compound researched mainly in the fields of physics and inorganic chemistry. The research on organogermanium compounds has increased in recent years, and the presentation or publication of research results or organogermanium compounds has become quite active. As a result, germanium and organogermanium compounds in particular are drawing attention in various technological fields.

For example, it is well-known in medical and pharmacological circles that carboxyethylgermanium sesquioxide $(GeCH_2CH_2COOH)_2O_3$, i.e. an organogermanium compound in which a propionic acid derivative of germanium and oxygen atom are bonded at a 2:3 ratio, is superior in physiological activities such as hypotensive activity, amyloidosis-alleviating activity and anti-tumor activity due to macrophage activation and interferon induction and yet shows no toxicity nor side effects. The above compound is being evaluated clinically.

The activator for osteoblasts of the present invention comprises an organogeramnium compound represented by the above, formula (I) as a basic active ingredient. This compound will be first explained. The compound of the formula (I) has, as a basic skeleton, a germylpropionic acid in which a propionic acid derivative having substituents $R_1$, $R_2$ and $R_3$ bonded to a germanium atom. In the compound, the germanium atom of the basic skeleton and oxygen atom are bonded at a 2:3 ratio.

The substituents $R_1$, $R_2$ and $R_3$ which may be the same or different, are independently a hydrogen atom, a lower alkyl group such as methyl, ethyl, propyl, butyl or the like, or an aryl group such as phenyl or the like. The substituents $R_1$ and $R_2$ are bonded to the $\alpha$-position of the germanium atom and the substituent $R_3$ is bonded to the $\beta$-position.

The organogermanium compound having the above structure can be produced according to various processes.

It can be produced, for example, by hydrolyzing a trihalogermylpropionic acid such as trichlorogermylpropionic acid already substituted with substituents $R_1$ to $R_3$, as shown by the following reaction formula.

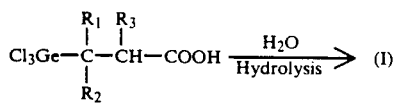

$$\text{Cl}_3\text{Ge}-\underset{\underset{R_2}{|}}{\overset{\overset{R_1}{|}}{C}}-\overset{\overset{R_3}{|}}{CH}-COOH \xrightarrow[\text{Hydrolysis}]{H_2O} \quad (I)$$

Meanwhile, as the basic group-containing compound forming a salt with the organogermanium compound, a basic amino acid is used.

The basic amino acid used in the present invention includes L-lysine, L-arginine, L-histidine, etc. It is believed that the bonding of the organogermanium compound and the basic amino acid in the present invention takes place between the carbonyl group COOH of the organogermanium compound and the amino or imino group of the basic amino acid.

The salt which is the active ingredient of the present activator can be obtained easily and at a high yield by reacting an organogermanium compound of the formula (I) with a basic amino acid according to the conventional process for an acid-base reaction. For example, a compound of the formula (I) is mixed with an equivalent amount of a basic amino acid; the mixture is dissolved in a minimum amount of water and heated; and the resulting solid is collected by filtration and cooled; or, the reaction mixture is concentrated thereby precipitating a crystal; or, the concentrate is mixed with an organic solvent such as ethanol thereby precipitating a salt and the salt is collected by filtration and dried.

The thus obtained salt as the active ingredient of the present activator, unlike the salt of the organogermanium compound of the formula (I) with an inorganic base, is highly crystalline and can be easily made into solid preparations such as tablets, granules, capsules and the like. Further, the salt has high solubility in water unlike the compound of the formula (I) and can be made directly into a solution containing the salt in an appropriate concentration (e.g. 2–10% by weight, preferably about 3–7% by weight in terms of the germanium compound).

The salt as the active ingredient of the present activator, in an aqueous solution, has a pH of about 7 suggesting the strong buffer action of the salt. Therefore, when the salt is administered orally the salt has a very low tendency to liberate liberating and precipitate an organogermanium compound coming in contact with gastric juices in the stomach; accordingly has very good absorption; and consequently is expected to show a high ratio of absorption by the human body and high bioavailability.

In contrast, when the salt of the organogermanium compound of the formula (I) with an inorganic base is administered orally in the form of an aqueous solution, there occurs an immediate liberation of the organogermanium compound (this compound is insoluble) by gastric juices, which results in a reduced ratio of absorption of the salt by the human body and reduced bioavailability of the salt. Further, in administering the salt of the organogermanium compound with an inorganic base such as a sodium or potassium base, the sodium or potassium ion is administered in an amount equivalent to the organogermanium compound, which adversely affects the normal ionic level in the human body.

Deviation of the sodium or potassium ion concentration in the human body from the normal level is believed to be a direct cause of hypertension and apoplexy. Thus, the salt of the organogermanium compound with an inorganic base of sodium, potassium or the like significantly reduces the advantages of the organogermanium compound, of showing substantially no side effects and of being suitable for administration in a large amount.

The activator for osteoblasts of the present invention can be administered orally or parenterally depending upon the condition of the disease. The present activator can be made into various forms conventionally employed in oral and parenteral administrations, such as solutions, powders, parvules, granules, tablets, coated tablets, capsules, injections, ointments, creams and the like. These forms can be produced by mixing a salt between an organogermanium compound of the formula (I) and a basic group-containing compound with any conventionally used additives such as diluting agents, fillers, binders, disintegrating agents, lubricants, perfumes, coloring agents, sterilized water and the like.

The agent of the present invention is administered, in the case of adults, one to several times a day in an amount of 10–100 mg/kg, preferably 30–70 mg/kg in terms of daily total dose depending upon the condition of disease.

The organogermanium compound used in the present activator has substantially no toxicity. The amino acid also used in the present activator as a basic group-containing compound not only is a natural component of the human body but also is used as a drug such as oral drug or injection; therefore, its safety, efficacy and stability are proven known and the use of the amino acid as a drug component poses no problem at all.

The present activator is used to activate osteoblasts. The osteoblasts are present in a cylindrical form on a surface of osteogenesis and from a monolayer thereon and, in osteogenesis, are believed to not only synthesize organic substrates such as collagen, glycoprotein and the like but also form substrate vesicles to deposit therein bone salts such as hydroxyapatite and the like. Application of the present agent to osteoblasts showed a direct activation effect for osteoblasts.

The present agent exhibits the above effect at a very low concentration. Further, the organogermanium compound used in the present agent has low toxicity. Thus, the present agent has a strong effect and high safety, can improve an imbalance between osteogenesis and bone resorption by activating osteoblasts, and can be utilized for the cure of osteal diseases such as osteoporosis and the like.

EXAMPLES

The present invention is explained in more detail below by way of Examples.

EXAMPLE 1

14.6 g of L-lysine and 16.9 g of carboxyethylgermanium sesquioxide were dissolved in a small amount of hot water while stirring. The undissolved solid was removed by filtration and the filtrate was added in small portions to a 10-fold volume of ethanol while stirring, whereby the formed salt was precipitated. The solution containing the salt precipitate was allowed to stand in a refrigerator to thoroughly precipitate the salt. The solution was filtered and the crystal collected was dried in a vacuum desiccator to obtain a desired product in a colorless crystalline fine powder form. Yield: 73% Melting point: above 270° C. (decomposed) The IR spectrum of the product is shown in FIG. 1.

EXAMPLE 2

Method

As osteoblasts to be cultured, there was used cloned MC3T3-E1 obtained from newly born mouse calvaria. These cells were planted in an α-MEM containing 10% of a fetal calf serum in a dish so that the cells were present in a proportion of $10^5$ per dish, and were cultured under a condition of 95% air and 5% $CO_2$ until the cells reached a confluent state.

Separate culturing was conducted in the same manner as above except that as the medium, there was used an α-MEM containing 0.3% of BSA and 10 μg/ml (in terms of final concentration) of the present activator obtained in Example 1, whereby the efficacy of the present activator was assayed.

Alkaline phosphatase was used as a yardstick of osteoblast activation, and alkaline phosphatases at 1, 2, 3 and 4 days after the start of culturing were measured. The reason for using alkaline phosphatase as a yardstick of osteoblast activation is that a higher cell activity produces a higher amount of alkaline phosphatase although the mechanism is unclear and this alkaline phosphatase is generally used as a yardstick of osteoblast activation.

Result

Figure 2:
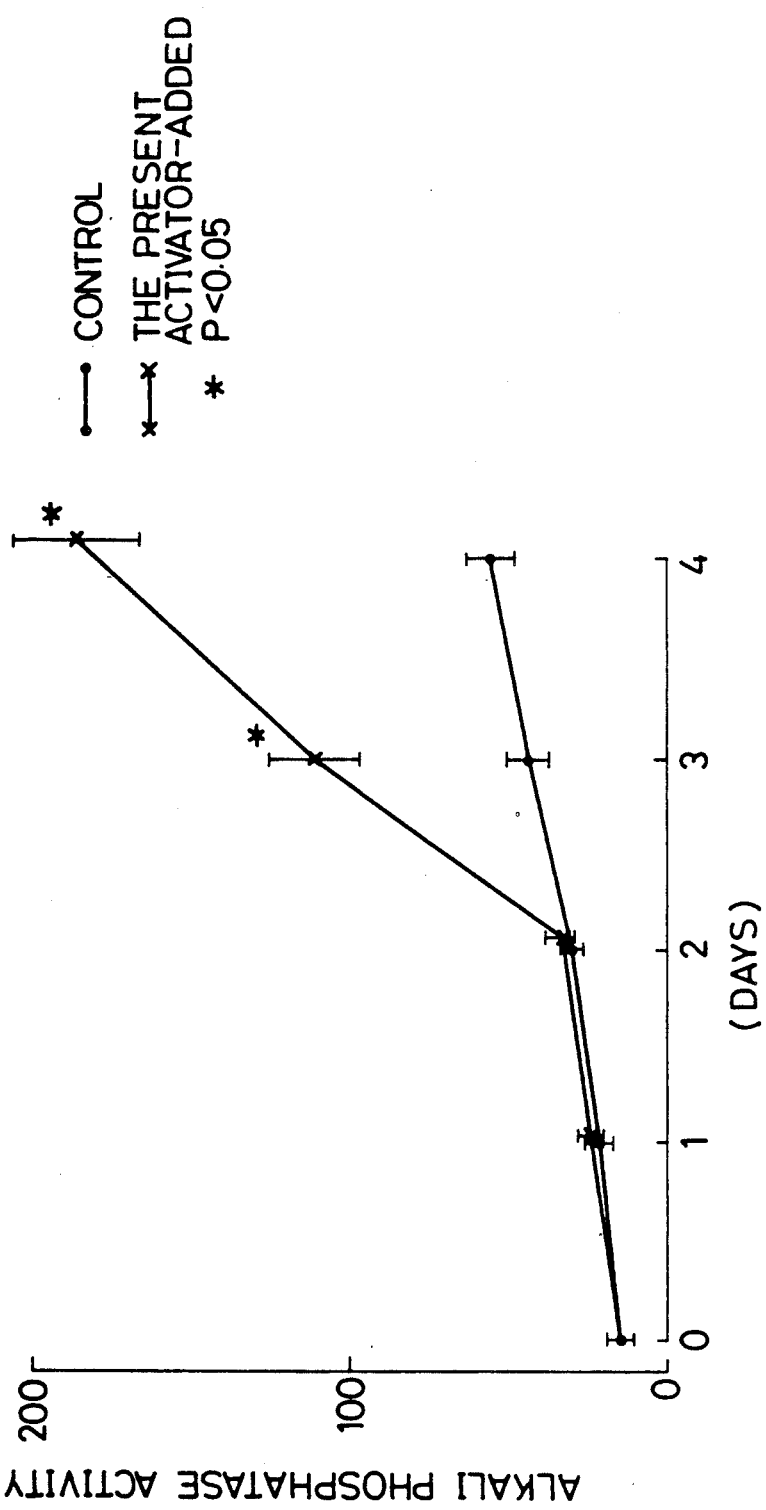
FIG. 2 is a graph showing a state in which cloned osteoblasts are activated by the present activator.

As shown in FIG. 2, the activity of MC3T3-E1 expressed in alkali phosphatase amount increased at the third to fourth day of culturing owing to the addition of the present activator, and there was seen a significant difference between the present activator-added case and the control.

EXAMPLE 3

Method

To each of 8 osteoporosis patients (all female, average age: 72 years old) was administered the present activator obtained in Example 1, in an amount of 6 capsules (each capsule contained 250 mg of the present activator) per day over a period of 15 weeks, and the amount of immunoreactive parathyroid hormone (i-PTH) in serum was measured by means of radioimmunoassay.

Result

Figure 3:
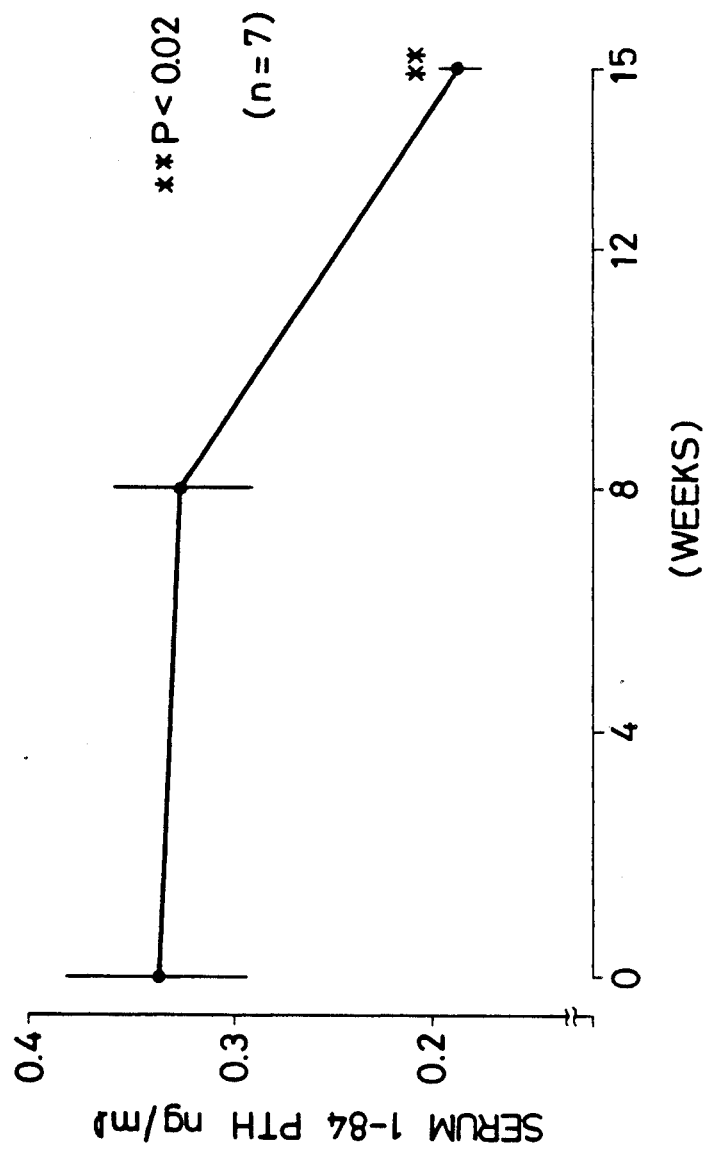
FIG. 3 is a graph showing a state in which the i-PTH value in human serum is reduced by the present activator.

As shown in FIG. 3, the i-PTH value after the administration of the present agent began to decrease in the 8th week after administration and decreased significantly in the 15th week after administration.

The reason for using i-PTH as a yardstick is that in osteoporosis, parathyroid hormone in blood is at a higher level in many cases and the examination of the relationship between bone amount and parathyroid hormone indicates that the bone amount and the parathyroid hormone are in a negative relationship.

Accordingly, the result of the above experiment suggests that the present activator is effective for curing osteoporosis by reducing the i-PTH in blood.

It was confirmed from the above experiments that the present activator increases the activity of cloned osteoblasts. Substantially the same results as above were obtained with the present activators using other compounds of the formula (I) as an active ingredient.

What is claimed is:

1. A method for activating osteoblasts comprising administering orally to a patient in need of such treatment a pharmaceutically effective amount of a salt between an organogermanium compound of formula (I):

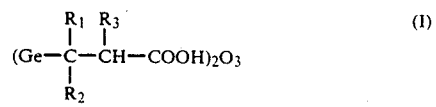

wherein $R_1$, $R_2$ and $R_3$ which are the same or different represent a hydrogen atom, a lower alkyl group or an aryl group, and a basic amino acid, to activate osteoblasts.

2. The method according to claim 1, wherein said lower alkyl group is a methyl or an ethyl group.

3. The method according to claim 1, wherein said basic amino acid is L-lysine.

4. The method according to claim 1, wherein said salt is administered at least once a day in an amount of 10 to 100 mg/kg.

5. The method according to claim 4, wherein said salt is administered at least once a day in an amount of 30 to 70 mg/kg.

* * * * *